(12) United States Patent
Moriguchi et al.

(10) Patent No.: US 8,404,887 B2
(45) Date of Patent: Mar. 26, 2013

(54) PROCESS FOR PRODUCING ACRYLIC ACID (75) Inventors: Toshimitsu Moriguchi, Suita (JP);
Yoshitaka Arita, Tsukuba (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 13/141,325

(22) PCT Filed: Dec. 24, 2009

(86) PCT No.: PCT/JP2009/071494
§ 371 (c)(1),
(2), (4) Date: Jun. 21, 2011

(87) PCT Pub. No.: WO2010/074177
PCT Pub. Date: Jul. 1, 2010

(65) Prior Publication Data
US 2011/0257355 A1   Oct. 20, 2011

(30) Foreign Application Priority Data

Dec. 26, 2008 (JP) .................. 2008-333737
Jul. 2, 2009 (JP) .................. 2009-157995

(51) Int. Cl.
*C07C 51/16* (2006.01)
*C07C 51/42* (2006.01)
*C08F 20/06* (2006.01)
(52) U.S. Cl. ...... 562/535; 562/531; 562/532; 526/317.1
(58) Field of Classification Search .................. None
See application file for complete search history.

(56) References Cited

U.S. PATENT DOCUMENTS

| 4,320,227 A | 3/1982 | Matsumoto et al. |
| 5,177,260 A | 1/1993 | Kawajiri et al. |
| 5,387,720 A | 2/1995 | Neher et al. |
| 5,739,392 A | 4/1998 | Tanimoto et al. |
| 5,817,865 A | 10/1998 | Machhammer et al. |
| 6,107,358 A | 8/2000 | Harada et al. |
| 6,174,978 B1 | 1/2001 | Hatsuda et al. |
| 6,241,928 B1 | 6/2001 | Hatsuda et al. |
| 6,541,665 B1 | 4/2003 | Bastiaensen et al. |
| 6,710,141 B1 | 3/2004 | Heide et al. |
| 6,867,269 B2 | 3/2005 | Sakamoto et al. |
| 6,906,159 B2 | 6/2005 | Dairoku et al. |
| 7,091,253 B2 | 8/2006 | Dairoku et al. |

(Continued)

FOREIGN PATENT DOCUMENTS

| JP | 53-82715 A | 7/1978 |
| JP | 5382715 | * 7/1978 |

(Continued)

OTHER PUBLICATIONS

Lucarelli et al., Applied Catalysis A: General 325 (2007) 244-250.*

(Continued)

*Primary Examiner* — Karl J Puttlitz (57) ABSTRACT

A process for producing acrylic acid of the present invention comprises the step of conducting gas-phase oxidative dehydrogenation of a composition containing propionaldehyde using a solid catalyst containing molybdenum and vanadium as essential components, thereby obtaining acrylic acid. The obtained acrylic acid is preferably purified by crystallization, and a monomeric component containing the purified acrylic acid is polymerized to thereby give a hydrophilic resin such as an absorbent resin and a water-soluble resin.

10 Claims, 3 Drawing Sheets

U.S. PATENT DOCUMENTS

| | | | |
|---|---|---|---|
| 7,179,875 B2 | 2/2007 | Fuchs et al. | |
| 7,396,962 B1 | 7/2008 | Dubois et al. | |
| 7,612,230 B2 * | 11/2009 | Shima et al. | 562/535 |
| 7,655,818 B2 | 2/2010 | Dubois et al. | |
| 7,910,771 B2 | 3/2011 | Dubois et al. | |
| 2002/0040095 A1 | 4/2002 | Dairoku et al. | |
| 2004/0110897 A1 | 6/2004 | Sakamoto et al. | |
| 2004/0186229 A1 | 9/2004 | Heide et al. | |
| 2005/0054788 A1 | 3/2005 | Dairoku et al. | |
| 2007/0021296 A1 | 1/2007 | Liang et al. | |
| 2007/0021630 A1 | 1/2007 | Liang et al. | |
| 2007/0129570 A1 | 6/2007 | Shima et al. | |
| 2008/0004408 A1 | 1/2008 | Stueven et al. | |
| 2008/0146852 A1 | 6/2008 | Dubois et al. | |
| 2008/0183013 A1 | 7/2008 | Dubois et al. | |
| 2008/0188681 A1 | 8/2008 | Liang et al. | |
| 2008/0214880 A1 * | 9/2008 | Dubois et al. | 585/500 |
| 2008/0242815 A1 | 10/2008 | Fukumoto | |
| 2010/0063233 A1 | 3/2010 | Shima et al. | |
| 2010/0069583 A1 | 3/2010 | Kasuga et al. | |

FOREIGN PATENT DOCUMENTS

| | | |
|---|---|---|
| JP | 5382715 A | 7/1978 |
| JP | 54-46705 A | 4/1979 |
| JP | 3-218334 A | 9/1991 |
| JP | 6-211724 A | 8/1994 |
| JP | 8-206504 A | 8/1996 |
| JP | 9-227445 A | 9/1997 |
| JP | 11-35519 A | 2/1999 |
| JP | 2002-519402 A | 7/2002 |
| JP | 2005-213225 A | 8/2005 |
| JP | 2008-115103 A | 5/2008 |
| JP | 2008-162907 A | 7/2008 |
| JP | 2008-530151 A | 8/2008 |
| JP | 2008-264766 A | 11/2008 |
| JP | 2008-538781 A | 11/2008 |
| WO | 01/38402 A1 | 5/2001 |
| WO | 2006/034806 A1 | 4/2006 |
| WO | 2006/087083 A2 | 8/2006 |
| WO | 2006/087084 A2 | 8/2006 |

OTHER PUBLICATIONS

Hashimoto et al., Relationship between activation energy of desorption of NH3 and Hammett acidity function, Shokubai, vol. 29, No. 6, pp. 406-409, 1987, Japan.

Sakamoto et al., Surface property of aluminum phosphate, Nippon Kagaku Kaishi, 1995(9), pp. 681-688, The Chemical Society of Japan, Japan.

European Patent Office, Extended European search report including the supplementary European search report and the European search opinion, Sep. 17, 2012, European Patent Office, Rijswijk, Netherlands.

Japanese Patent Office, Notice of Submission of Information by Third Parties, Jan. 15, 2013, Japanese Patent Office, Tokyo, Japan.

* cited by examiner

PROCESS FOR PRODUCING ACRYLIC ACID

This is the U.S. national phase of International Application No. PCT/JP2009/071494, filed Dec. 24, 2009, which claims priority from Japanese Patent Application No. 2008-333737 filed Dec. 26, 2008 and Japanese Patent Application No. 2009-157995 filed Jul. 2, 2009.

TECHNICAL FIELD

The present invention relates to a process for producing acrylic acid with high purity from glycerin as a low material efficiently.

BACKGROUND ART

Acrylic acid, which is used as a raw material of an absorbent resin and the like, has been industrially widely produced by gas-phase oxidation of acrolein obtained by gas-phase oxidation of propylene.

In recent years, production of acrylic acid by gas-phase oxidation of a product which has been obtained by gas-phase dehydration of glycerin has been disclosed (refer to Patent Literature 1).

In addition, production of acrolein by dehydration of glycerin is disclosed (refer to Patent Literature 2). The acrolein obtained by this production differs from acrolein which is obtained by gas-phase oxidation of propylene in terms of kinds and quantities of byproducts. Therefore, in order to produce acrylic acid by conducting conventionally-known gas-phase oxidation of a composition containing such acrolein, it is described to be preferable that acrolein is purified by employing a conventionally-known technique (refer to Patent Literature 2).

Further, it is disclosed of a process for producing acrylic acid, comprising the steps of producing allyl alcohol from glycerin and conducting gas-phase oxidation of the obtained allyl alcohol to produce acrylic acid (refer to Patent Literature 3).

CITATION LIST

Patent Literature

Patent Literature 1
Japanese Unexamined Patent Application Publication No. 2005-213225
Patent Literature 2
International Publication WO 2006/087084
Patent Literature 3
Japanese Unexamined Patent Application Publication No. 2008-162907

SUMMARY OF INVENTION

Technical Problem

As byproducts in the process for producing acrylic acid from propylene, acetaldehyde, acetic acid and the like are known to be produced in the step of producing acrolein, for example, and formic acid, acetic acid, propionic acid and the like are known to be produced in the step of producing acrylic acid, for example. Meanwhile, as byproducts in the process for producing acrylic acid from glycerin derived from biodiesel, propionaldehyde, phenol, 1-hydroxyacetone, 2-methoxyacetone, methoxypropanal and the like are known to be produced in the step of producing acrolein, and formic acid, acetic acid, propionic acid, pyruvic acid, 3-methoxypropionic acid and the like are known to be produced in the step of producing acrylic acid, for example. Moreover, in the process for producing acrylic acid from glycerin, a considerably large amount of impurities is produced as byproducts, as compared with that in the process for producing acrylic acid from propylene. Thus, in the process for producing acrylic acid from glycerin, it is required to purify acrolein or acrylic acid efficiently.

The purity of acrylic acid affects production of a hydrophilic resin, and it is known, for example, that presence of acetic acid or propionic acid in the acrylic acid possibly causes a problem of odor of the resin. In the process for producing acrylic acid from glycerin, since a considerably large amount of organic acids such as acetic acid and propionic acid is produced as byproducts, as compared with that in the process for producing acrylic acid from propylene, a technique for efficiently purifying acrylic acid is required.

Acrylic acid produced by the above-described producing process can be, in general, purified by distillation or crystallization. However, according to the investigations by the present inventors, it has been found that since impurities as byproducts are produced in a considerably large quantity in the process for producing acrylic acid from glycerin as described above, purification by crystallization is easy to be operated and preferable while purification by distillation is complex to be operated and induces increase of the production cost. Further, it has also been found that purification by crystallization is effective to remove organic acids such as propionic acid, which are substances causing odor of the resin.

In view of the above circumstances, an object of the present invention is to provide a process for producing acrylic acid with high purity from glycerin as a low material efficiently.

Solution to Problem

Conventionally, it has not been known that acrylic acid can be produced by conducting gas-phase oxidative dehydrogenation of propionaldehyde. In addition, propionaldehyde is not contained in an acrolein-containing composition which is an oxidation product of propylene and industrially widely used for producing acrylic acid. Therefore, it has been considered to be preferable to separate propionaldehyde and acrolein for producing acrylic acid by oxidation of acrolein from a composition containing propionaldehyde and acrolein, which is a dehydration product of glycerin.

However, propionaldehyde and acrolein belong to the same category of aldehyde compounds, and moreover, the boiling point of propionaldehyde, that is 48° C., is close to the boiling point of acrolein, that is 52° C., so that propionaldehyde and acrolein are difficult to be separated by a conventionally-known method such as distillation or using a treatment agent (e.g., hydrazine).

The present inventors have intensively studied to a process for producing acrylic acid from a composition containing propionaldehyde, and as a result, they have found that a composition containing acrylic acid and propionic acid can be obtained by gas-phase oxidative dehydrogenation of the composition containing propionaldehyde using a solid catalyst containing molybdenum and vanadium as essential components. Therefore, acrylic acid with high purity can be efficiently produced without separating propionaldehyde from the composition containing propionaldehyde and acrolein prepared by dehydration of glycerin. Further, it has been found that acrylic acid and propionic acid in the obtained composition are efficiently separated by purification of crystallization, compared with purification of distillation. Therefore, since propionic acid, which causes the odor, can be removed to a detection limit or lower from the obtained acrylic acid, the obtained acrylic acid has the comparable polymerization property to acrylic acid obtained by the process of producing from propylene, and a hydrophilic resin such as, for example, an absorbent resin and a water-soluble resin, which is produced from the obtained acrylic acid, is free from odor and has the same physical properties as a conventional one.

That is, the present invention provides a process for producing acrylic acid, comprising the step of conducting gas-phase oxidative dehydrogenation of a composition containing propionaldehyde using a solid catalyst containing molybdenum and vanadium as essential components.

In the process for producing acrylic acid of the present invention, the composition may contain at least acrolein in addition to propionaldehyde. Further, the composition may contain propionaldehyde and acrolein prepared by dehydration of glycerin. In addition, the process for producing acrylic acid of the present invention preferably further comprises the step of crystallizing acrylic acid from a composition containing acrylic acid prepared by the gas-phase oxidative dehydrogenation to purify.

The present invention also provides a process for producing a hydrophilic resin such as an absorbent resin and a water-soluble resin, comprising the step of polymerising a monomeric component including acrylic acid produced by the process described above.

Advantageous Effects of Invention

According to the present invention, acrylic acid is obtained from a composition containing propionaldehyde, and further, acrylic acid is also obtained from a composition containing propionaldehyde and acrolein without separating propionaldehyde therefrom. In addition, impurities contained in acrylic acid obtained by gas-phase oxidative dehydrogenation and gas-phase oxidation of a composition containing propionaldehyde and acrolein prepared from glycerin can be efficiently removed by crystallization; and therefore, acrylic acid having the comparable grade to the acrylic acid obtained by a conventional process for producing acrylic acid from propylene via acrolein can be obtained. Moreover, the obtained acrylic acid is excellent in polymerizability and suitably used for producing an absorbent resin.

DESCRIPTION OF THE PREFERRED EMBODIMENTS

<<Process for Producing Acrylic Acid>>

A Process for producing acrylic acid of the present invention, that may be hereinafter referred to as a "producing process of the present invention", comprises the step of conducting gas-phase oxidative dehydrogenation of a composition containing propionaldehyde using a solid catalyst containing molybdenum and vanadium as essential components.

<Raw Material>

Acrylic acid is produced from propionaldehyde by the gas-phase oxidative dehydrogenation, as the present inventors have found. Therefore, a raw material used for the producing process of the present invention is not particularly limited as long as it is a composition containing at least propionaldehyde. Further, according to the producing process of the present invention, acrylic acid can be produced by gas-phase catalytic oxidation of acrolein in addition to the gas-phase oxidative dehydrogenation of propionaldehyde. Therefore, the composition containing acrolein in addition to propionaldehyde may be used as the raw material in the producing process of the present invention. Such a composition containing both propionaldehyde and acrolein can be prepared, for example, by dehydration of glycerin.

<Solid Catalyst>

The solid catalyst used in the producing process of the present invention is a molybdenum-vanadium catalyst which contains molybdenum and vanadium as essential components, and a solid catalyst used for producing acrylic acid by gas-phase oxidation of acrolein is preferably used.

Specific examples of the solid catalyst include, for example, a molybdenum-vanadium catalyst prepared by the steps of evaporating a solution containing ammonium molybdate, ammonium metavanadate, copper nitrate, ammonium paratungstate and zirconium oxide to dryness to obtain a solid matter, pulverizing and forming the solid matter, and drying and calcinating the formed material (refer to Example 1 in Japanese Unexamined Patent Application Publication No. 3-218334); and a molybdenum-vanadium catalyst prepared by the steps of depositing a solution containing ammonium paramolybdate, ammonium metavanadate, vanadium trioxide, copper nitrate, copper (I) oxide and antimony trioxide on a carrier of α-alumina and drying and calcinating the obtained solution-deposited carrier (refer to Example 1 in Japanese Unexamined Patent Application Publication No. 8-206504).

A shape of the solid catalyst is not particularly limited, and examples of the shape of the solid catalyst include, for example, a spherical shape, a cylindrical shape, a ring shape, a saddle shape. Size of the solid catalyst is generally about 0.1 mm to 10 mm in diameter.

<Gas-Phase Oxidative Dehydrogenation and Gas-Phase Oxidation>

In the producing process of the present invention, gas-phase oxidative dehydrogenation of a composition containing propionaldehyde is conducted. The composition of a raw material may contain at least acrolein in addition to propionaldehyde. In this case, the composition of the raw material is, for example, a composition containing propionaldehyde and acrolein, which is prepared by dehydration of glycerin. In the case where the composition contains acrolein in addition to propionaldehyde, acrylic acid is produced by simultaneously conducting gas-phase oxidative dehydrogenation of propionaldehyde and gas-phase oxidation of acrolein.

Reaction conditions for conducting the gas-phase oxidative dehydrogenation and the gas-phase oxidation may be the same as those of a conventionally-known process for producing acrylic acid from acrolein. For example, a reaction raw material gas containing the composition of the raw material, oxygen and an inert gas, which is inactive to the reaction and added to adjust the gas concentration, is used as a raw material gas. Examples of the oxygen include, for example, pure oxygen and oxygen-enriched air, however, oxygen of air is preferably used in view of economical aspect. Examples of the inert gas include, for example, steam, nitrogen and carbon dioxide. Further, it is preferred to reuse all or a part of the residual gas which is obtained after a product of the oxidative dehydrogenation has been collected or all or a part of the gas which is obtained after organic matters in the residual gas has been combusted, as the inert gas in view of economical aspect. It is generally known that steam is effective to reduce the combustion range formed by organic matters and oxygen, and thus, steam is preferably contained in the inert gas.

The sum concentration of propionaldehyde and acrolein in the reaction raw material gas is generally in the range of 0.1 volume % to 15 volume %, and preferably in the range of 0.4 volume % to 12 volume %. The concentration of oxygen in the reaction raw material gas is generally in the range of 0.5 volume % to 25 volume %, and preferably in the range of 2 volume % to 20 volume %. The concentration of steam in the reaction raw material gas is generally in the range of 0 volume % to 50 volume %, and preferably 3 volume % to 45 volume %. Examples of the residue of the reaction raw material gas include, for example, nitrogen and carbon dioxide.

A flow rate of the reaction raw material gas, a gas flow rate per unit volume of the catalyst (GHSV), is generally in the range of 500 $h^{-1}$ to 20,000 $h^{-1}$, and preferably in the range of 1,000 $h^{-1}$ to 10,000 $h^{-1}$. Reaction temperature is generally in the range of 180° C. to 350° C., and preferably in the range of 200° C. to 330° C. Reaction pressure is generally in the range of 0.001 MPa to 1 MPa, and preferably in the range of 0.01 MPa to 0.5 MPa.

<Dehydration of Glycerin>

For preparing the composition containing propionaldehyde and acrolein by dehydration of glycerin, a conventionally-known process can be employed. Specifically, homogeneous or heterogeneous liquid-phase reaction in which glycerin of a liquid state or glycerin in a solution is contacted with a solid acid catalyst under ordinary or increased pressure condition may be employed, or gas-phase reaction in which glycerin gas or glycerin-containing gas is contacted with a solid acid catalyst may be employed. Among these reactions, the gas-phase reaction of the latter is particularly preferable.

In the gas-phase reaction of the latter, a raw material gas containing glycerin is contacted with a solid acid catalyst in a reactor which is arbitrarily selected from a fixed-bed reactor, a moving-bed reactor, a fluidized-bed reactor, and the like to produce the composition containing propionaldehyde and acrolein.

The solid acid catalyst is not particularly limited, as long as it is a catalyst having a solid acid. Examples of the solid acid catalyst include, for example, a crystalline metallosilicate; a metal oxide; a clay mineral; a catalyst in which a mineral acid is supported on an inorganic carrier, a catalyst in which a metal salt of mineral acid is supported on an inorganic carrier.

Specifically, examples of the crystalline metallosilicate include a compound which contains, for example, at least one kind of T atoms selected from the group consisting of Al, B, Fe and Ga, and has a crystalline structure such as, for example, LTA, CHA, FER, MFI, MOR, BEA or MTW. Examples of the metal oxide include metal oxides such as, for example, $Al_2O_3$, $TiO_2$, $ZrO_2$, $SnO_2$ and $V_2O_5$, and complex oxides such as, for example, $SiO_2$—$Al_2O_3$, $SiO_2$—$TiO_2$, $TiO_2$—$WO_3$ and $WO_3$—$ZrO_2$. Examples of the clay mineral include, for example, bentonite, kaolin and montmorillonite. Examples of the catalyst in which a mineral acid is supported on an inorganic carrier include, for example, a catalyst in which phosphoric acid, sulfuric acid or the like is supported on α-alumina, silica, zirconium oxide, titanium oxide or the like. Examples of the catalyst in which a metal salt of mineral acid is supported on an inorganic carrier include, for example, a catalyst in which $MgSO_4$, $Al_2(SO_4)_3$, $K_2SO_4$, $AlPO_4$, $Zr_3(PO_4)_4$ or the like is supported on α-alumina, silica, zirconium oxide, titanium oxide or the like.

In addition, a solid acid disclosed in International Publications WO 2006/087083 and WO 2006/087084, that is zirconium oxide supporting phosphoric acid, sulfuric acid or tungsten oxide, may be used.

Among these catalysts, a highly stable solid acid catalyst is preferred, since it can be put in oxidation or reduction atmosphere of high temperature during the dehydration or a regeneration treatment; and crystalline metallosilicates, metal oxides, clay minerals, and the like are much preferred. As the crystalline metallosilicate, HZSM-5, which contains Al as the T atom and has a MFI structure, is preferable; and as the metal oxide, crystalline phosphate compound is preferable, and aluminum phosphate is particularly preferable.

Concerning acid strength of HZSM-5, it is known that HZSM-5 has a strong acidity having peaks about −9 and −16 in Hammett acid strength parameter $H_0$ (refer to the document: Kenji Hashimoto et al., Shokubai, vol. 29, No. 6, pp. 406-409, 1987). In addition, it is known that acid strength of aluminum phosphate varies depending on a preparing method thereof and a crystalline structure, and aluminum phosphate has weak solid acidity of +1.5 to +4.8 in Hammett acid strength parameter $H_0$ (refer to the document: Kiyoko Sakamoto et al., Nippon Kagaku Kaishi, 1995(9), pp. 681-688).

In the gas-phase reaction, the catalyst with lowered activity can be regenerated by bringing the catalyst into contact with a gas containing an oxidative gas such as oxygen at high temperature. A manner of bringing the catalyst into contact with the gas is not particularly limited; and the contact may be done after the catalyst is taken out of the reactor, or may be done by exchanging the gas to be introduced into the reactor in which the dehydration is conducted. In the case where the dehydration is conducted in a fixed-bed reactor, the latter in which the catalyst is not needed to be taken out and refilled is simple and thus recommended.

In the case where oxygen is used as the oxidative gas which is used for the regeneration treatment, use of oxygen of air is economical; and an inert gas such as steam, nitrogen and carbon dioxide may be accompanied with oxygen. Particularly, in the case where there is a risk of abrupt heat generation due to the fact that air contains about 20 volume % of oxygen, it is recommended to use an inert gas for adjusting the concentration of oxygen. Before or after the regeneration treatment, for removing or decreasing excess organic matters remaining in the system or residual oxygen after the regeneration treatment, purging the system by an inert gas such as nitrogen may be conducted.

The regenerated catalyst can be used as a catalyst for synthesizing acrolein again when being contacted with the reaction raw material gas.

In the gas-phase reaction, glycerin partial pressure in the reaction raw material gas at an inlet of the reactor is generally 30 kPa or less, preferably 25 kPa or less, more preferably 20 kPa or less, and even more preferably 15 kPa or less. The lower glycerin partial pressure is preferred; however, in order to secure constant productivity, the following methods are needed: (I) lowering the reaction pressure or (II) adding a large amount of diluent components together. Considering from an industrial viewpoint, a highly air-tight and pressure resistant reactor and a large scale pressure reducing apparatus are needed in the method (I); and there is a problem that it costs much to collect the produced acrolein and to use a large amount of diluent components and power cost is increased along with the pressure loss in the method (II). Therefore, from the industrial viewpoint, the glycerin partial pressure in the reaction raw material gas at the inlet of the reactor is preferably 0.01 kPa or more, more preferably 0.1 kPa or more, and even more preferably 1 kPa or more.

Here, the glycerin partial pressure means a partial pressure of glycerin gas in the reaction raw material gas at the inlet of the reactor. For example, in the case where glycerin concentration in the reaction raw material gas is 100 volume %, the glycerin partial pressure is equivalent to the pressure of the reaction raw material gas at the inlet of the reactor. In the case where the reaction raw material gas contains a gaseous component other than glycerin, the glycerin partial pressure is determined depending on the glycerin concentration in the reaction raw material gas, of total pressure of the reaction raw material gas at the inlet of the reactor.

The total pressure of the reaction raw material gas at the inlet of the reactor is generally 0.01 kPa or more, preferably 0.1 kPa or more, and more preferably 1 kPa or more. The upper limit of the total pressure is not particularly limited as long as the reaction gas exists as a gas at the inlet of the reactor, and the total pressure is generally 500 kPa or less, preferably 300 kPa or less, and more preferably 200 kPa or less.

Generally, the glycerin partial pressure is not more than 30 kPa, and therefore, when the pressure of the reaction raw material gas is 30 kPa or more at the inlet of the reactor, the reaction raw material gas inevitably contains a diluent component other than glycerin. In addition, even in the case where the total pressure of the reaction raw material gas is 30 kPa or less, the reaction raw material gas may contain a diluent component.

Examples of the diluent component include, for example, steam, nitrogen and air. Among these diluent components, steam is preferable, since adding steam brings in an advantageous effect on a catalyst lifetime and an acrolein yield.

In the case where steam is used as the diluent component, steam may be accompanied with glycerin from the step of purifying glycerin, may be newly added, or the combination of them may be employed. As to the preferable amount of steam, steam partial pressure is generally 5 times or less as much as the glycerin partial pressure in the reaction raw material gas at the inlet of the reactor, preferably 3 times or less as much as that, and more preferably 2 times or less as much as that. When the amount of steam is adjusted like this, an advantageous effect on a catalyst lifetime and an acrolein yield is brought in and a heavy load is not imposed on the step of purifying the reaction product, and thus preferable.

In the case where the gas-phase reaction is conducted under ordinary or increased pressure condition, gas such as nitrogen which is non-condensable, that is, not liquefied under ordinary temperature and ordinary pressure condition, and non-oxidative can be employed as the diluent component other than steam, for example. However, in the case where collecting propionaldehyde and acrolein produced in the reaction is conducted, it is necessary to take account of collecting efficiency in the collecting step, and therefore, as to the amount of the diluent component other than steam, the partial pressure of the diluent component other than steam is generally 20 times or less as much as the glycerin partial pressure in the reaction raw material gas at the inlet of the reactor, preferably 15 times or less as much as that, and more preferably 12 times or less as much as that.

Space velocity of the reaction raw material gas including glycerin and the diluent component at the inlet of the reactor is generally in the range of 70 $h^{-1}$ to 50,000 $h^{-1}$, preferably in the range of 70 $h^{-1}$ to 25,000 $h^{-1}$, more preferably in the range of 100 $h^{-1}$ to 12,000 $h^{-1}$, and even more preferably in the range of 125 $h^{-1}$ to 12,000 $h^{-1}$.

Reaction temperature of the gas-phase reaction is preferably 250° C. or higher and 500° C. or lower, more preferably 300° C. or higher and 450° C. or lower, even more preferably 330° C. or higher and 440° C. or lower. When the reaction temperature is too low, a conversion rate of glycerin is lowered and productions of propionaldehyde and acrolein are decreased, and thus it is not preferred. On the other hand, when the reaction temperature is too high, yields of propionaldehyde and acrolein are remarkably decreased, and thus it is not preferred.

When an organic compound other than glycerin is contained in the reaction raw material gas in a small amount except the above-described diluent component, the effect of shortening a so-called induction period where yields of propionaldehyde and acrolein are low at the beginning of the reaction may be provided. Examples of the preferable organic compound include acrolein, acetaldehyde, acetic acid, acrylic acid, methanol, ethanol, aliphatic acids, aliphatic acid esters.

In the case where the organic compound other than glycerin is contained in the reaction raw material gas, deterioration of a catalyst activity may be accelerated when the organic compound is too much contained. Therefore, the content of the organic compound relative to the total of organic compounds contained in the reaction raw material gas is preferably 20 mass % or less, more preferably 10 mass % or less, and even more preferably 5 mass % or less.

Further, as the diluent component other than steam, oxydizing gas such as oxygen can be contained in the diluent component. When the diluent component contains the oxydizing gas, accumulation of carbonaceous matters on the catalyst is decreased, and the effect of suppressing the deterioration of the catalyst activity may be provided. Nevertheless, when the oxydizing gas is too much contained, yields of propionaldehyde and acrolein are decreased due to a combustion reaction, and thus it is not preferred. In the case of using oxygen as the oxydizing gas, the content of oxygen is preferably 15 volume % or less as oxygen concentration or 3.5 times or less as much as glycerin concentration in the reaction raw material gas at the inlet of the reactor, whichever is lower.

In the case of conducting the reaction using the diluent component under reduced pressure condition, steam and the like are preferably used for reducing load on a decompression device, since steam has lower boiling point than glycerin and condenses at ordinary temperatures and pressures.

In the case of using glycerin derived from biodiesel as the raw material, the composition which is prepared by dehydration of glycerin and contains propionaldehyde and acrolein may be used as-is to produce acrylic acid; however, the composition contains phenol, 1-hydroxyacetone, 2-methoxyacetone, methoxypropanal and the like as byproducts, which cause deterioration of the catalyst activity, decrease of the yield, or production of byproducts such as formic acid, acetic acid, propionic acid, pyruvic acid, 3-methoxypropionic acid in acrylic acid, and hence, the composition which has been purified may be used. The purification can be conducted by a conventionally-known method, and examples of the purification include a method of distilling a condensed liquid of the reaction composition or a collection liquid obtained by using a collection solvent, and a method of using a purification apparatus provided with a collection column and a diffusion column, which is disclosed in Japanese Unexamined Patent Application Publication No. 2008-115103. In the case where the composition is not purified, impurities in acrylic acid may be removed by purifying acrylic acid in the subsequent step.

In view of simplifying the process and lowering production cost, it is preferred that the composition is not purified to be used.

<Crystallization Step>

In the producing process of the present invention, a gaseous substance containing acrylic acid and propionic acid is obtained by the gas-phase oxidative dehydrogenation of the composition containing propionaldehyde using the solid catalyst containing molybdenum and vanadium as essential components. This gaseous substance is liquefied by cooling condensation or being collected by solvent, and if necessary, water or the collection solvent contained in the liquefied substance is removed by a conventionally-known method (e.g., distillation), and thereafter, a crystallization step is conducted to obtain acrylic acid with high purity.

The crystallization step can be conducted by a conventionally-known method which can separate propionaldehyde from crude acrylic acid, such as a method disclosed in, for example, Japanese Unexamined Patent Application Publication Nos. 9-227445 and 2002-519402.

The crystallization step is the step of crystallizing acrylic acid by supplying crude acrylic acid to a crystallization apparatus to obtain purified acrylic acid. As a method of crystallization, a conventionally-known crystallization method can be employed, and the method is not particularly limited; however, the crystallization may be performed in one or more stages by using a continuous or batch type crystallization apparatus. If necessary, the obtained crystallized acrylic acid may be further subjected to purification such as washing or sweating to obtain purified acrylic acid with further improved purity.

Examples of the continuous crystallization apparatus include a crystallization apparatus in which a crystallization part, a solid-liquid separation part and a crystal purification part are united (e.g., BMC (Backmixing Column Crystallizer) manufactured by Nippon Steel Chemical Co., Ltd.; continuous melting and purifying system manufactured by Tsukishima Kikai Co., Ltd.), and a crystallization apparatus in combination with a crystallization part (e.g., CDC (Cooling Disc Crystallizer) manufactured by GMF GOUDA), a solid-liquid separation part (e.g., a centrifugal separator or a belt filter), and a crystal purification part (e.g., KCP (Kureha Crystal Purifier) manufactured by Kureha Engineering Co., Ltd.).

Examples of the batch type crystallization apparatus include a layer-crystallizing apparatus (a dynamic crystallization apparatus) manufactured by Sulzer Chemtech Ltd. and a static crystallization apparatus manufactured by BEFS PROKEM.

Dynamic crystallization is a method for conducting crystallization by using a dynamic crystallization apparatus which is equipped with, for example, a tubular crystallizer provided with a temperature control mechanism for conducting crystallizing, sweating and melting, a tank for recovering a mother liquid after sweating, and a circulation pump for supplying crude acrylic acid to the crystallizer, and in which the crude acrylic acid is transferred by the circulation pump from a storage tank installed under the crystallizer to an upper part of the tubular crystallizer. Meanwhile, static crystallization is a method for conducting crystallization by using a static crystallization apparatus which is equipped with, for example, a tubular crystallizer provided with a temperature control mechanism for conducting crystallizing, sweating and melting, wherein the crystallizer has a discharge valve at a lower part thereof, and a tank for recovering a mother liquid after sweating.

Specifically, crude acrylic acid of a liquid phase is introduced into a crystallizer, whereby acrylic acid of the liquid phase is solidified to be deposited on a cooling face (a tubular wall face). When the mass of the solid deposited on the cooling face reaches preferably 10 mass % to 90 mass %, and more preferably 20 mass % to 80 mass %, of the crude acrylic acid introduced into the crystallizer, the liquid is immediately discharged out of the crystallizer to separate the solid and the liquid. The liquid may be discharged by either of a method of pumping up the liquid (dynamic crystallization) or a method of flowing the liquid out of the crystallizer (static crystallization). Meanwhile, the solid is taken out of the crystallizer, and then, may be purified by washing or sweating in order to further improve the purity.

In the case where the dynamic crystallization or the static crystallization is performed in multistage, the crystallization can be conducted advantageously by employing the counter-flow principle. In this case, the crystallized acrylic acid is separated from the remaining mother liquid in each stage and supplied to the stage in which acrylic acid with higher purity is produced. Meanwhile, the remaining mother liquid is supplied to the stage in which acrylic acid with lower purity is produced.

In the dynamic crystallization, when the purity of acrylic acid is low, the crystallization becomes difficult; whereas, in the static crystallization, the crystallization is easily performed even when the purity of acrylic acid is low, since contact time of the remaining mother liquid with the cooling face is prolonged and effect of the temperature tends to be transferred easily, compared with the dynamic crystallization. Therefore, for improving recovery efficiency of acrylic acid, the final remaining mother liquid in the dynamic crystallization may be subjected to the static crystallization to be further crystallized.

The number of stages for the crystallization to be needed depends on the demand of the degree of purity, and the number of stages needed for obtaining acrylic acid with high purity is generally 1 to 6 stages, preferably 2 to 5 stages, more preferably 2 to 4 stages for purification stage (dynamic crystallization) and generally 0 to 5 stages, preferably 0 to 3 stages for stripping stage (dynamic crystallization and/or static crystallization). In general, stages in which acrylic acid with higher purity than that of supplied crude acrylic acid is obtained are all purification stages, and stages other than these stages are all stripping stages. The stripping stage is conducted for recovering acrylic acid contained in the remaining mother liquids generated from the purification stages. The striping stage is not necessarily provided, and, in the case where low boiling point components are separated from the remaining mother liquid of the crystallization apparatus by using a distillation column, for example, the stripping stage may be omitted.

Even in the case of employing either the dynamic crystallization or the static crystallization, the crystallized acrylic acid obtained in the crystallization step may be used as-is as a product, or may be further purified by washing or sweating to obtain a product, if necessary. On the other hand, the remaining mother liquid discharged from the crystallization step may be taken out of the system.

<<Process for Producing Hydrophilic Resin>>

A process for producing a hydrophilic resin of the present invention comprises the step of polymerizing a monomeric component including acrylic acid produced by the process for producing acrylic acid of the above. Thus, acrylic acid obtained by the producing process of the present invention can be utilized as a raw material of a hydrophilic resin such as an absorbent resin and a water-soluble resin.

However, acrylic acid obtained by the process for producing acrylic acid from glycerin contains a large amount of organic acids such as formic acid, acetic acid and propionic acid as byproducts, which possibly cause odor or coloration of the hydrophilic resin, compared with acrylic acid obtained by a process for producing acrylic acid from propylene. Thus, it is important to purify the obtained acrylic acid. Among impurities contained in the acrylic acid, propionic acid has similar boiling point to acrylic acid, and therefore, when propionic acid is contained in large amount, purification of acrylic acid by distillation becomes difficult. Accordingly, in the process for producing a hydrophilic resin of the present invention, acrylic acid from which propionic acid has been removed by purification of crystallization is preferably used.

When acrylic acid obtained by the producing process of the present invention is used as a raw material for producing a hydrophilic resin such as an absorbent resin and a water-soluble resin, polymerization reaction is easily controlled, quality of the obtained hydrophilic resin becomes stabilized, and various performances such as absorption ability and dispersion performance of an inorganic material are improved.

For producing the absorbent resin, for example, acrylic acid and/or its salt obtained by the producing process of the present invention is used as a main component (preferably 70 mol % or more, and more preferably 90 mol % or more) of monomeric components, and further about 0.001 mol % to 5 mol % (value relative to acrylic acid) of a crosslinking agent and about 0.001 mol % to 2 mol % (value relative to the monomeric components) of a radical polymerization initiator are used to conduct crosslinking polymerization, and then the product is dried and pulverized to obtain the absorbent resin.

Here, the absorbent resin means water-swellable and water-insoluble polyacrylic acid having a crosslinked structure, which forms water-insoluble hydrogel containing preferably 25 mass % or less, more preferably 10 mass % or less of a water-soluble component (a water-soluble fraction) by absorbing deionized water or normal saline solution in an amount of 3 times or more, preferably 10 times to 1000 times as much as the weight of the polymer itself. Specific examples and measurement methods of physical properties of the absorbent resin like this is described in U.S. Pat. Nos. 6,107,358, 6,174,978, 6,241,928 and the like.

Preferable producing method in view of improving productivity are disclosed in, for example, U.S. Pat. Nos. 6,867,269, 6,906,159 and 7,091,253, International Publications Nos. WO 01/038402 and WO 2006/034806, and the like.

A sequence of the steps for producing the absorbent resin from acrylic acid as a starting raw material by neutralization, polymerization, drying and the like are, for example, as follows.

A portion of acrylic acid obtained by the producing process of the present invention is supplied to the producing process of the absorbent resin through a line. In the producing process of the absorbent resin, acrylic acid is introduced into a neutralization step, a polymerization step and a drying step to be conducted desired treatments, thereby producing the absorbent resin. For improving various physical properties, any treatments may be conducted, and, for example, a crosslinking step may be conducted during the polymerization or after the polymerization.

The neutralization step is optional, and, for example, a method of mixing a powder or aqueous solution of a predetermined amount of a basic substance with acrylic acid or polyacrylic acid (salt) is exemplified; however, a conventionally-known method may be employed without any limitation. The neutralization step may be conducted either before the polymerization or after the polymerization or both before and after the polymerization. As the basic substance to be used for neutralizing acrylic acid or polyacrylic acid (salt), conventionally-known basic substances such as, for example, (hydrogen) carbonates, alkali metal hydroxides, ammonia, and organic amines may be used appropriately. Neutralization ratio of the polyacrylic acid is not particularly limited and may be adjusted to be an optional neutralization ratio (e.g., an optional value in the range of 30 mol % to 100 mol %).

A polymerization method in the polymerization step is not particularly limited, and conventionally-known polymerization methods such as polymerization using a radical polymerization initiator, radiation polymerization, polymerization by radiating electron beam or active energy beam, and ultraviolet polymerization using a photosensitizer may be employed. Further, various conditions such as kinds of the polymerization initiator and polymerization conditions may be selected appropriately. Of course, conventionally-known additives such as crosslinking agents, other monomers, water-soluble chain transfer agents and hydrophilic polymers can be added, if necessary.

Acrylate polymer obtained by the polymerization, that is, absorbent resin, is subjected to the drying step. A drying method is not particularly limited, and a conventionally-known drying means such as a hot-air drier, a fluidized-bed drier, and a Nauta drier may be used for appropriately drying at a desired drying temperature, preferably at the temperature in the range of 70° C. to 230° C.

The absorbent resin obtained in the drying step may be used as-is, or may be used after granulation and pulverization into a desired shape and surface-crosslinking, or may be used after post-treatment corresponding to the usage such as adding conventionally-known additives including a reducing agent, a fragrance and a binder.

EXAMPLES

The present invention is hereinafter described more specifically by reference to Examples; however, the present invention is not limited to these Examples, and can be put into practice after appropriate modifications or variations within a range meeting the gist of the present invention, all of which are included in the technical scope of the present invention.

Experiment Example 1

Oxidation of Propionaldehyde

A fixed-bed reactor was provided by filling a reaction tube (inner diameter of 25 mm, length of 500 mm) made of stainless steel with 20 mL of an oxidation catalyst, and the reactor was installed in a niter bath at 230° C. Then, propionaldehyde-containing gas was introduced into the reactor. Here, as the propionaldehyde-containing gas, a mixed gas consisting of 2 volume % of propionaldehyde, 12 volume % of oxygen, 37 volume % of water and 49 volume % of nitrogen was introduced at a space velocity (GHSV) of 1,800 hr$^{-1}$. After 1 hour from introducing the propionaldehyde-containing gas, effluent gas from the reactor was condensed by cooling to recover, thereby obtaining an acrylic acid-containing composition.

The oxidation catalyst was prepared as follows. Into 2,500 mL of water which was stirred while heating, 350 g of ammonium paramolybdate, 116 g of ammonium metavanadate, and 44.6 g of ammonium paratungstate were dissolved, and then, 1.5 g of vanadium trioxide was further added thereto. Separately, into 750 mL of water which was stirred while heating, 87.8 g of copper nitrate was dissolved, and then, 1.2 g of copper (I) oxide and 29 g of antimony trioxide were added thereto. Thus obtained two solutions were mixed, 1,000 mL of spherical α-alumina having a diameter of 3 mm to 5 mm as a carrier was fed thereto, and then, the resultant mixture was evaporated to dryness while stirring to obtain a catalyst precursor. The catalyst precursor was calcinated at 400° C. for 6 hours to give the oxidation catalyst for producing acrylic acid. The supported metal element composition of the oxidation catalyst for producing acrylic acid was $Mo_{12}V_{6.1}W_1Cu_{23}Sb_{1.2}$.

Experiment Example 2

Oxidation of a Mixed Gas Containing Propionaldehyde and Acrolein

Reaction was carried out in the same manner as in Experiment Example 1, except that a mixed gas containing propionaldehyde and acrolein, which consists of 0.2 volume % of propionaldehyde, 1.8 volume % of acrolein, 12 volume % of oxygen, 37 volume % of water and 49 volume % of nitrogen, was used as substitute for the propionaldehyde-containing gas.

The acrylic acid-containing compositions obtained in the above Experiment Examples 1 and 2 were quantitatively analyzed by gas chromatograph to obtain the conversion rates of propionaldehyde, the conversion rates of acrolein, the yields of acrylic acid, and the yields of propionic acid. These results are shown in Table 1. Here, the yield of acrylic acid and the yield of propionic acid shown in Table 1 were calculated based on propionaldehyde or a sum of molar quantity of propionaldehyde and acrolein in the reaction raw material gas.

TABLE 1

|  | Experiment Example 1 | Experiment Example 2 |
| --- | --- | --- |
| Concentration of propionaldehyde | 2.0 vol % | 0.2 vol % |
| Concentration of acrolein | — | 1.8 vol % |
| Conversion rate of propionaldehyde | 99.6 mol % | 98.9 mol % |
| Conversion rate of acrolein | — | 98.7 mol % |
| Yield of acrylic acid | 3.1 mol % | 82.3 mol % |
| Yield of propionic acid | 78.9 mol % | 8.9 mol % |

As shown in Table 1, it was found that acrylic acid was produced from propionaldehyde by the producing process of the present invention. It was also found that acrylic acid was produced from the mixed gas containing propionaldehyde and acrolein.

Experiment Example 3

Productions of Propionaldehyde and Acrolein by Dehydration of Glycerin

A $ZnAl_2O_4$ catalyst used for synthesizing propionaldehyde and acrolein from glycerin by dehydration was prepared as follows.

40 g of alumina (boehmite, manufactured by SASOL Ltd.; trade name: Catapal B) was fed to a porcelain mortar, and further 12.5 g of zinc oxide (special grade, manufactured by Wako Pure Chemical Industries, Ltd.) was added thereto to be well mixed. Into the thus obtained mixture of alumina and zinc oxide, the aqueous solution obtained by adding 2.8 g of nitric acid to 40 g of ion-exchanged water was added and well mixed. After mixing, the resultant mixture was concentrated until it was made into a paste-like product on a hot-water bath. The resultant concentrated product was fed to a porcelain dish and dried at 100° C. for 4 hours and at 150° C. for 3 hours under air current, and further calcinated at 700° C. for 2 hours under air current. The resulting calcinated product was pulverized and sieved to obtain a catalyst with a particle size of 0.7 mm to 2.0 mm.

A fixed-bed reactor was provided by filling a reaction tube (inner diameter of 10 mm, length of 500 mm) made of stainless steel with 15 mL of the above catalyst, and the reactor was installed in a niter bath at 360° C.

Then, glycerin-containing gas was introduced into the reactor. Here, as the glycerin-containing gas, a mixed gas consisting of 27 volume % of glycerin, 34 volume % of water and 39 volume % of nitrogen was introduced at a space velocity (GHSV) of 630 $hr^{-1}$. During the time from 0.5 hours to 1 hour and from 2.5 hours to 3 hours from the start of introducing the glycerin-containing gas, the gas flown out of the reactor was absorbed in acetonitrile in a gas scrubbing bottle to recover a composition containing propionaldehyde and acrolein.

The obtained recovered solutions after the reaction were quantitatively analyzed by gas chromatography, and it was found that the conversion rate of glycerin was 100 mol %, the yield of propionaldehyde was 10 mol %, and the yield of acrolein was 41 mol % during the time from 0.5 hours to 1 hour from the start of introducing the glycerin-containing gas, and the conversion rate of glycerin was 100 mol %, the yield of propionaldehyde was 8 mol %, and the yield of acrolein was 51 mol % during the time from 2.5 hours to 3 hour from the start.

Experiment Example 4

Productions of Propionaldehyde and Acrolein by Dehydration of Glycerin

A $TiO_2/ZrO_2$ catalyst (the amount of supported $TiO_2$ was 7.4 mass %) used for synthesizing propionaldehyde and acrolein from glycerin by dehydration was prepared as follows.

22.8 g of titanium tetraisopropoxide (special grade, manufactured by Wako Pure Chemical Industries, Ltd.) was fed to a porcelain mortar, and 80.0 g of zirconium oxide (manufactured by Daiichi Kigenso Kagaku Kogyo Co., Ltd.; RSC-HP) was further added thereto to be well mixed. After mixing, the resultant mixture was evaporated into dryness on a hot-water bath while well stirring.

The resultant product was dried at 120° C. overnight, calcinated at 900° C. for 3 hours under air current, and then, the calcinated product was pulverized and sieved to obtain a catalyst with a particle size of 0.7 mm to 2.0 mm.

A fixed-bed reactor was provided by filling the reaction tube made of stainless steel shown in Experiment Example 3 with 15 mL of the above catalyst, and dehydration reaction of glycerin was carried out in the same condition as in Experiment Example 3.

During the time from 0.5 hours to 1 hour and from 2.5 hours to 3 hours from the start of introducing the glycerin-containing gas, the gas flown out of the reactor was absorbed in acetonitrile in a gas scrubbing bottle to recover a composition containing propionaldehyde and acrolein.

The obtained recovered solutions after the reaction were quantitatively analyzed by gas chromatography, and it was found that the conversion rate of glycerin was 99 mol %, the yield of propionaldehyde was 9 mol %, and the yield of acrolein was 40 mol % during the time from 0.5 hours to 1 hour from the start of introducing the glycerin-containing gas, and the conversion rate of glycerin was 100 mol %, the yield of propionaldehyde was 6 mol %, and the yield of acrolein was 42 mol % during the time from 2.5 hours to 3 hour from the start.

As shown in Experiment Examples 3 and 4, compositions containing propionaldehyde and acrolein were produced from glycerin, and further, as shown in Experiment Example 2, acrylic acid was produced from propionaldehyde contained in these compositions; and hence, it was found that acrylic acid was able to be produced from glycerin with high yield by supplying propionaldehyde in these compositions to the producing process of acrylic acid without separation.

Experiment Examples 5 to 10

Crystallization Step for Separating Propionic Acid from Crude Acrylic Acid

As shown in Experiment Examples 1 and 2, acrylic acid can be produced by oxidation of propionaldehyde and oxidation of a mixed gas containing propionaldehyde and acrolein; however, the thus obtained crude acrylic acid contains propionic acid as a major byproduct. Therefore, the present inventors examined a method for efficiently separating propionic acid from the crude acrylic acid.

First, as Experiment Example 5, 120 g of crude acrylic acid having composition shown in Table 2 as a mother liquid was put into a glass bottle and rapidly cooled to solidify the entirety thereof, and then, the resultant solid matter was melted while being immersed in a warm water in such a manner that a trace mount of the solid matter could remain. Next, the glass bottle was gradually cooled to −6° C. to grow a crystal, and after 20 hours, the crystal was separated from the liquid by suction filtration. The separated crystal was put into another glass bottle and slowly sweated to reduce the size thereof, and then, the crystal was separated from the liquid and melted to be analyzed its composition by gas chromatography. Further, another 5 experiments were conducted in the same manner except that the composition of the mother liquid and the cooling temperature were changed, and the results are shown in Table 2.

TABLE 2

| Experiment Example No. | Composition of mother liquid (mass %) | | Composition of crystal (mass %) | | Cooling temperature (° C.) |
|---|---|---|---|---|---|
| | Acrylic acid | Propionic acid | Acrylic acid | Propionic acid | |
| 5 | 79.7 | 20.3 | 95.4 | 4.7 | −6 |
| 6 | 89.3 | 10.7 | 97.9 | 2.1 | −2 |
| 7 | 95.3 | 4.7 | 99.0 | 1.0 | 3 |
| 8 | 98.2 | 1.8 | 99.5 | 0.5 | 7 |
| 9 | 99.2 | 0.8 | 99.8 | 0.2 | 10 |
| 10 | 99.7 | 0.3 | 99.9 | 0.1 | 12 |

Figure 1:
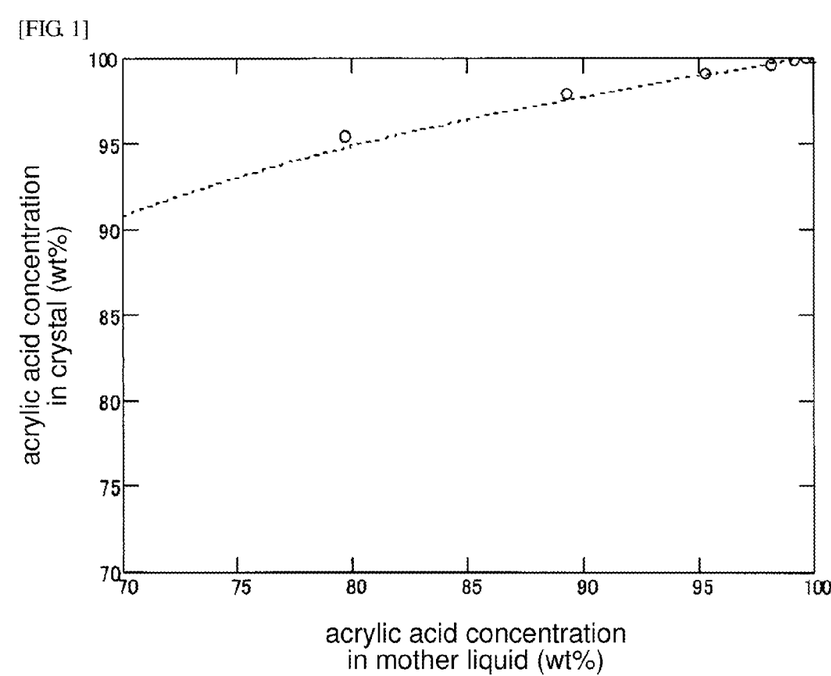
FIG. 1 shows a solid-liquid line chart which shows the correlation of acrylic acid concentrations in mother liquids and those in crystals obtained in Experimental Examples 5 to 10.

As shown in the result of Table 2, since the acrylic acid concentration in the crystal became higher than that in the mother liquid, it was found that the crude acrylic acid can be highly purified by the crystallization step. FIG. 1 shows a solid-liquid line chart which shows the correlation of acrylic acid concentrations in the mother liquids and those in the crystals. The solid-liquid line (a dotted line) shown in FIG. 1 was created by polynomial approximation from the data (circles) of the acrylic acid concentrations in the mother liquid and the crystal shown in Table 2.

Figure 2:
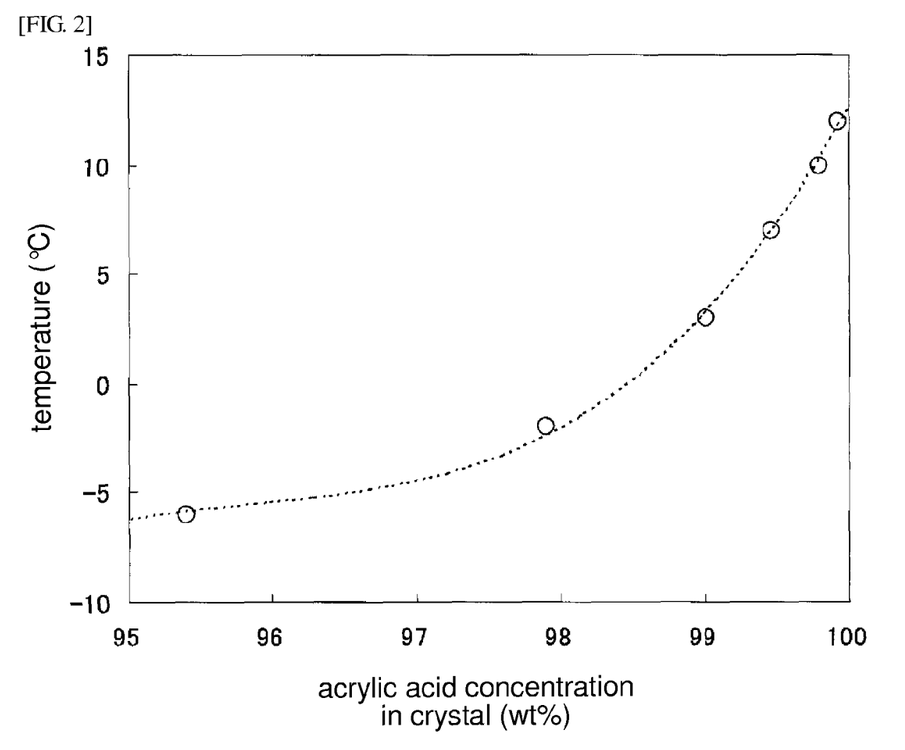
FIG. 2 shows a concentration curve chart which shows the correlation of acrylic acid concentrations in crystals and temperatures of the crystals obtained in Experimental Examples 5 to 10.

FIG. 2 shows a concentration curve chart which shows the correlation of acrylic acid concentrations in the crystals and temperatures of the crystals. The concentration curve (a dotted line) was created by polynomial approximation from the data (circles) of the acrylic acid concentrations in the crystals shown in Table 2.

Next, specific examples of highly purifying crude acrylic acid were simulated based on the solid-liquid line shown in FIG. 1 and the concentration curve shown in FIG. 2, and the results are explained.

Calculation Example 1

Batch Method

Crude acrylic acid containing 3.8 mass % of propionic acid as a mother liquid is cooled in the range of −2.3° C. to 10.0° C. to be deposited as a crystal and kept at the same temperature, and then, the crystal is separated from the liquid by suction filtration. The thus separated crystal is entirely melted, and crystallization operations are repeated in the same manner as the above. In this case, acrylic acid with a purity of 99.8% can be obtained by the third crystallization operation, as shown in Table 3.

TABLE 3

| | Mother liquid | First crystallization | Second crystallization | Third crystallization |
|---|---|---|---|---|
| Acrylic acid (mass %) | 96.2 | 98.9 | 99.6 | 99.8 |
| Propionic acid (mass %) | 3.8 | 1.1 | 0.4 | 0.2 |
| Temperature (° C.) | — | −2.3 | 7.7 | 10.0 |

Calculation Example 2

Continuous Method

Figure 3:
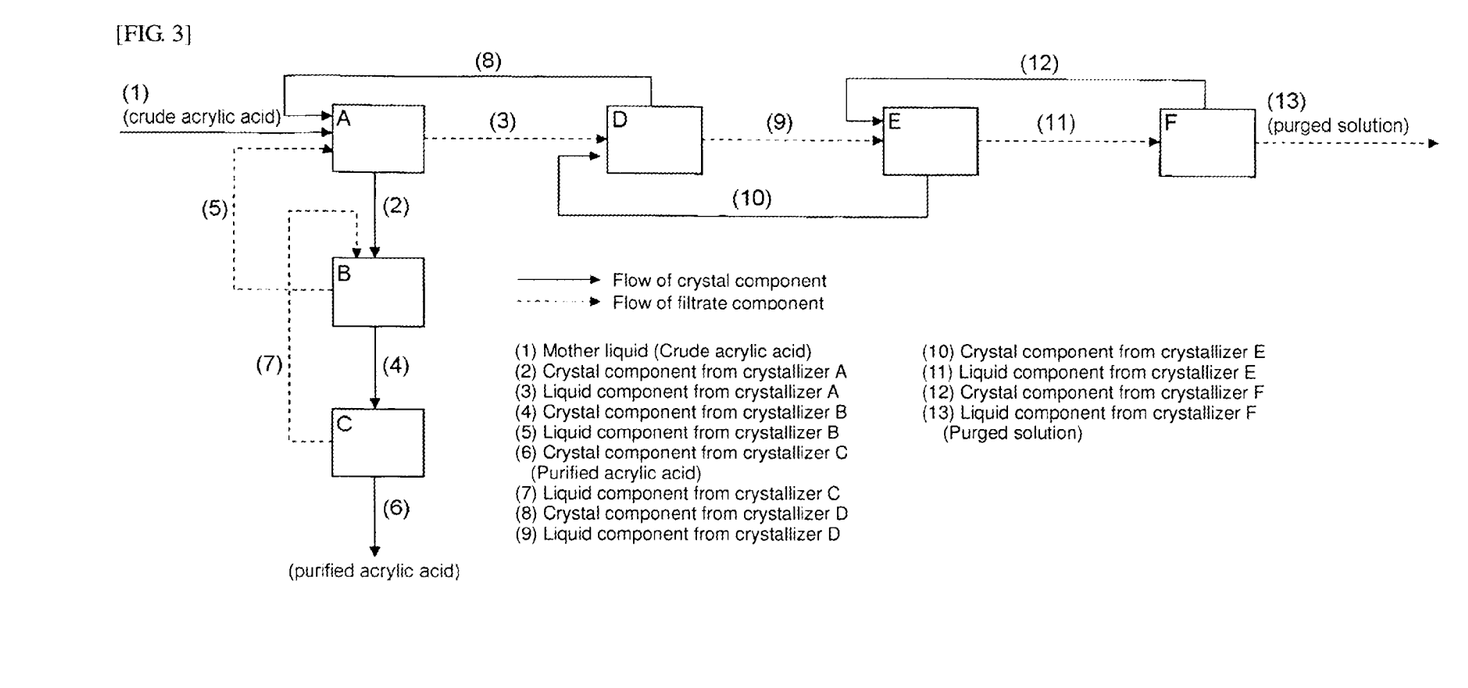
FIG. 3 shows a flowchart of one embodiment of a continuous method for separating propionic acid from crude acrylic acid.

Crude acrylic acid containing 2.0 mass % of propionic acid as a mother liquid is supplied at 1000 g/h to the crystallizer A, and the crystallization step is conducted continuously in accordance with the flowchart shown in FIG. 3. In this case, purified acrylic acid with a purity of 99.9% can be obtained at 928 g/h from the crystallizer C. Further, acrylic acid in which propionic acid is concentrated to be 26.4 mass % can be extracted at 72 g/h as a purged solution (a remaining mother liquid) from the crystallizer F. The compositions of the crystals and the filtrates in the respective steps are shown in Table 4.

TABLE 4

| | Mother liquid (1) | Crystallizer A | | Crystallizer B | | Crystallizer C | | Crystallizer D | | Crystallizer E | | Crystallizer F | |
|---|---|---|---|---|---|---|---|---|---|---|---|---|---|
| | | Crystal (2) | Filtrate (3) | Crystal (4) | Filtrate (5) | Crystal (6) | Filtrate (7) | Crystal (8) | Filtrate (9) | Crystal (10) | Filtrate (11) | Crystal (12) | Filtrate (13) |
| Acrylic acid (mass %) | 98.0 | 99.6 | 96.9 | 99.8 | 98.9 | 99.9 | 99.6 | 99.0 | 94.3 | 98.1 | 87.9 | 95.8 | 73.6 |
| Propionic acid (mass %) | 2.0 | 0.5 | 3.1 | 0.2 | 1.1 | 0.1 | 0.4 | 1.0 | 5.7 | 1.9 | 12.1 | 4.2 | 26.4 |
| Temperature (° C.) | 25 | 7 | | 10 | | 12 | | 3 | | −2 | | −6 | |

As is clear from Experiment Examples 5 to 10, crude acrylic acid could be highly purified by the crystallization step. Further, as is clear from Calculation Examples 1 and 2, propionic acid can be efficiently separated from crude acrylic acid, whichever the batch method or the continuous method for the crystallization step was employed. Therefore, it is understood that when the crystallization step is employed for purifying the composition containing acrylic acid obtained by gas-phase oxidative dehydrogenation of a composition containing propionaldehyde, acrylic acid with high purity can be obtained efficiently.

Experiment Example 11

Production of Acrylic Acid from Glycerin

Acrylic acid was produced from glycerin by the following steps.

(1) First reaction step: Glycerin was dehydrated to obtain a composition containing propionaldehyde and acrolein.

(2) First purification step: The reaction product obtained in the step (1) was purified to obtain a composition containing propionaldehyde and acrolein which is able to be supplied to a second reaction.

(3) Second reaction step: The composition obtained in the step (2) was oxidized to obtain a reaction product containing crude acrylic acid.

(4) Second purification step: The reaction product obtained in the step (3) was distilled to give crude acrylic acid and the crude acrylic acid is purified by crystallization to obtain acrylic acid.

(1) First reaction step (A Catalyst for the First Reaction)

Boron phosphate catalyst used for the first reaction is prepared as follows. A powder of boron phosphate (reagent manufactured by Johnson Matthey) was calcinated at 800° C. for 5 hours under air current, and the calcinated powder was finely pulverized in an agate mortar. The obtained finely pulverized product was put into a cylindrical mold made of vinyl chloride (outer diameter of 48 mm, inner diameter of 40 mm, and thickness of 5 mm) and pressurized and compacted with a compression molding machine by applying a pressure of about 20 ton (compression molding). The obtained compact molded product was taken out of the cylindrical mold and pulverized and sieved to obtain a catalyst for the first reaction with a particle diameter of 0.7 mm to 2.0 mm.

(Dehydration Reaction)

A fixed-bed reactor was provided by filling a reaction tube (inner diameter of 25 mm, length of 500 mm) made of stainless steel with 50 mL of the above catalyst, and the reactor was installed in a niter bath at 360° C.

A condenser was installed at an outlet of the reactor, and cooling water at about 4° C. was introduced thereinto. The pressure of the reaction system was reduced to 62 kPa by a vacuum pump, while adjusting the pressure using a constant vacuum apparatus. Then, a glycerin-containing gas was introduced into the reactor. As the glycerin-containing gas, a mixed gas consisting of 44 volume % of glycerin and 56 volume % of water was introduced at a space velocity (GHSV) of 420 hr$^{-1}$. The glycerin-containing gas was introduced intermittently for 20 hours, and the gas flowing out of the reactor was entirely condensed by the condenser and recovered in a receiver cooled by an ice bath. The weight of the recovered reaction product was 939 g, which corresponded to 99 mass % of the supplied raw material.

The obtained reaction product was quantitatively analyzed by gas chromatograph, and as a result, it was found that the reaction product contained 34 mass % of acrolein, 0.5 mass % of propionaldehyde, 6.4 mass % of 1-hydroxyacetone, 44 mass % of water and 15 mass % of heavy components.

(2) First Purification Step

The reaction product obtained in the step (1) was supplied at 0.12 kg/h to a thin film distiller, which was operated in the conditions of normal pressure, 85° C. of wall temperature on which a liquid film was formed, and 300 rpm of blade rotation speed, and a distillate containing 42 mass % of acrolein, 0.6 mass % of propionaldehyde, 4 mass % of 1-hydroxyacetone and 51 mass % of water (that is, a composition containing propionaldehyde and acrolein) was obtained at 0.11 kg/h from the top of the distiller.

(3) Second Reaction Step

A fixed-bed reactor was provided by filling a reaction tube (inner diameter of 25 mm, length of 500 mm) made of stainless steel with 50 mL of the oxidation catalyst prepared in Experiment Example 1, and the reactor was installed in a niter bath at 260° C. Then, the composition obtained in the step (2) was supplied to the reactor. A condenser was installed at an outlet of the reactor, and cooling water at about 15° C. was introduced thereinto. A mixed gas consisting of 6.5 volume % of acrolein, 0.09 volume % of propionaldehyde, 0.46 volume % of 1-hydroxyacetone, 6 volume % of oxygen, 13 volume % of water and 74 volume % of nitrogen was introduced as a propionaldehyde-containing gas at a space velocity (GHSV) of 1,900 hr$^{-1}$. The composition containing propionaldehyde and acrolein was introduced intermittently for 22 hours from the start of the reaction, and the gas flown out of the reactor was condensed by the condenser and recovered in a receiver cooled by an ice bath and in a cold trap subsequently installed.

The weight of the recovered reaction product which contains crude acrylic acid was 620 g, which corresponded to 95 mass % of the supplied raw material. Based on quantitatively analysis of gas chromatograph, it was found that the reaction product contained 62 mass % of crude acrylic acid, 0.1 mass % of propionic acid, 1 mass % of formic acid, 3 mass % of acetic acid and 34 mass % of water.

In the production of acrylic acid using glycerin as a raw material, it was found that the amounts of byproducts of organic acids such as propionic acid, formic acid and acetic acid were increased compared with the conventional process for producing acrylic acid using propylene as a raw material.

(4) Second Purification Step

The reaction product obtained in the step (3) was supplied at 0.2 kg/h to the fifth stage of a distillation column having 10 stages and continuously distilled under the conditions of a refluxing ratio of 1 and a distillation amount from the top of the column of 0.067 kg/h. As a result, crude acrylic acid having composition of 86.6 mass % of acrylic acid, 0.1 mass % of propionic acid, 2.4 mass % of acetic acid, 0.04 mass % of formic acid and 10.9 mass % of water was obtained at 0.133 kg/h from the bottom of the column. Crystallization operation was conducted by cooling the crude acrylic acid as a mother liquid to a temperature range of −5.8° C. to room temperature (about 15° C.) to form a crystal, keeping at the same temperature, and then, separating the crystal from the liquid by suction filtration. The separated crystal was melted, and a portion of the crystal was sampled for analysis and the rest thereof was processed by the crystallization operation, in which the rest was cooled as a mother liquid to a temperature range of 4.8° C. to room temperature (about 15° C.) to form a crystal, kept at the same temperature, and then, the crystal was separated from the liquid by suction filtration. According to the crystallization operations repeated two times in total, acrylic acid with a purity of 99.9 mass % or higher was obtained finally. The results are shown in Table 5. The total amount of propionic acid and acetic acid was below the detection limit (1 ppm).

TABLE 5

|  | Mother liquid | First crystallization | Second crystallization |
|---|---|---|---|
| Acrylic acid (mass %) | 86.6 | 98.8 | 99.9 |
| Propionic acid (mass %) | 0.1 | N.D. | N.D. |
| Acetic acid (mass %) | 2.4 | 0.3 | 0.02 |
| Water (mass %) | 10.9 | 0.9 | 0.08 |
| Temperature (° C.) | — | −5.8 | 4.9 |

N.D. means a value below the detection limit (1 ppm).

Experiment Example 12

Production of an Absorbent Resin

Acrylic acid containing acetic acid and propionic acid in a total amount of 200 ppm by mass, which was obtained in the second crystallization operation in Experiment Example 11, was mixed with a polymerization inhibitor to give acrylic acid containing 60 ppm by mass of the polymerization inhibitor. Thus obtained acrylic acid was added to NaOH aqueous solution, which had been separately prepared from sodium hydroxide containing 0.2 ppm by mass of iron, under cooling condition (solution temperature 35° C.) to be neutralized at 75 mol %. The content of iron in the acrylic acid and the water was under a detection limit, and therefore, the iron content in the monomer was about 0.07 ppm by mass based on the calculated value.

Into the obtained 35 mass % sodium acrylate aqueous solution, which has a neutralization ratio of 75 mol %, 0.05 mol % (relative to the sodium acrylate aqueous solution) of polyethylene glycol diacrylate as an internal crosslinking agent was dissolved to obtain a monomeric component. 350 g of the monomeric component was fed to a cylindrical vessel with a volume of 1 L, and nitrogen was blown at 2 L/minute into the vessel for 20 minutes to expel the air. Then, an aqueous solution containing 0.12 g/mol (relative to the monomeric component) of sodium persulfate and 0.005 g/mol (relative to the monomeric component) of L-ascorbic acid was added thereto while being stirred by a stirrer to start polymerization. After starting of the polymerization, the stifling was stopped and static aqueous solution polymerization was conducted. The temperature of the monomeric component reached peak polymerization temperature of 108° C. after about 15 minutes (polymerization peak time), and then, polymerization was proceeded for 30 minutes. Subsequently, the resulting polymer material was taken out of the cylindrical vessel to obtain a hydrated gel-like crosslinked polymer.

The obtained hydrated gel-like crosslinked polymer was segmented at 45° C. by a meat chopper (hole diameter 8 mm) and dried at 170° C. for 20 minutes by a hot-air drier. Further, the dried polymer (solid matter: about 95%) was pulverized by a roll mill and classified by a JIS standard sieve into those having a particle diameter of 300 μm to 600 μm, thereby obtaining a polyacrylic acid absorbent resin (neutralization ratio 75%).

Acrylic acid obtained by the producing process of the present invention has the comparable polymerization property to acrylic acid obtained by the process of producing acrylic acid from propylene, and the obtained hydrophilic resin is free from odor and has the same physical properties as a conventional one.

According to the present invention, acrylic acid can be produced at high efficiency from glycerin. Further, if purification is conducted by crystallization, propionic acid, which lowers a polymerization property, can be removed to a detection limit or lower from the thus obtained acrylic acid; and therefore, the thus obtained acrylic acid has the comparable polymerization property to acrylic acid obtained by the process of producing acrylic acid from propylene, and the hydrophilic resin such as, for example, an absorbent resin and a water-soluble resin, which is produced from the obtained acrylic acid, is free from odor and has the same physical properties as a conventional one. Accordingly, the present invention can enormously contribute to the technical fields where acrylic acid is used.

The invention claimed is:

1. A process for producing acrylic acid, comprising the step of conducting gas-phase oxidative dehydrogenation of a composition containing propionaldehyde using a molybdenum-vanadium solid catalyst containing molybdenum and vanadium as essential components to produce acrylic acid and propionic acid, wherein one of acrylic acid and propionic acid is the main product.

2. The process according to claim 1, wherein
the composition contains at least acrolein in addition to propionaldehyde.

3. The process according to claim 1, wherein
the composition contains propionaldehyde and acrolein prepared by dehydration of glycerin.

4. The process according to claim 1, further comprising the step of crystallizing acrylic acid from a composition containing acrylic acid produced by the gas-phase oxidative dehydrogenation to purify the acrylic acid.

5. A process for producing a hydrophilic resin, comprising the step of polymerizing a monomeric component including acrylic acid produced by the process according to claim 1.

6. A process for producing an absorbent resin, comprising the step of polymerizing a monomeric component including acrylic acid produced by the process according to claim 1.

7. The process according to claim 2, wherein the composition contains propionaldehyde and acrolein prepared by dehydration of glycerin.

8. The process according to claim 2, further comprising the step of crystallizing acrylic acid from a composition containing acrylic acid produced by the gas-phase oxidative dehydrogenation to purify the acrylic acid.

9. A process for producing a hydrophilic resin, comprising the step of polymerizing a monomeric component including acrylic acid produced by the process according to claim 2.

10. A process for producing an absorbent resin, comprising the step of polymerizing a monomeric component including acrylic acid produced by the process according to claim 2.

* * * * *